United States Patent
Zhang et al.

(10) Patent No.: US 11,200,671 B2
(45) Date of Patent: Dec. 14, 2021

(54) REFERENCE IMAGE GUIDED OBJECT DETECTION IN MEDICAL IMAGE PROCESSING

(71) Applicant: International Business Machines Corporation, Armonk, NY (US)

(72) Inventors: Shi Lei Zhang, Beijing (CN); Qing Wang, Beijing (CN); Jie Zhang, Beijing (CN); Yubo Li, Beijing (CN); Ke Jin, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 116 days.

(21) Appl. No.: 16/731,736

(22) Filed: Dec. 31, 2019

(65) Prior Publication Data

US 2021/0201487 A1    Jul. 1, 2021

(51) Int. Cl.
*G06T 7/00* (2017.01)
*G06K 9/62* (2006.01)
*G16H 50/20* (2018.01)
*G16H 30/40* (2018.01)
*G16H 30/20* (2018.01)
(Continued)

(52) U.S. Cl.
CPC .......... *G06T 7/0014* (2013.01); *G06F 16/538* (2019.01); *G06K 9/6215* (2013.01); *G06K 9/6232* (2013.01); *G06K 9/6254* (2013.01); *G06K 9/6256* (2013.01); *G06K 9/6269* (2013.01); *G06N 3/04* (2013.01); *G16H 30/20* (2018.01); *G16H 30/40* (2018.01); *G16H 50/20* (2018.01); *G06K 2209/055* (2013.01);
(Continued)

(58) Field of Classification Search
CPC ....... G06T 2210/12; G06T 2207/20084; G06T 7/0014; G06N 3/08; G06N 3/04; G06K 2209/27; G06K 2209/055; G06K 9/6269; G06K 9/6256; G06K 9/6254; G06K 9/6232; G06K 9/6215; G06F 16/538; G16H 30/40; G16H 50/20; G16H 30/20
See application file for complete search history.

(56) References Cited

U.S. PATENT DOCUMENTS 7,949,173 B2 *  5/2011  Zhou ........................ G06K 9/00
                                                         382/131
8,331,637 B2 * 12/2012  Bar-Aviv ............... G16H 70/60
                                                         382/128
(Continued)

OTHER PUBLICATIONS

Daniel S. Fritsch, Stephen M. Pizer, Liyun Yu, Valen Johnson, and Edward L. Chaney, "Localization and Segmentation of Medical Image Objects using Deformable Shape Loci," IPMI 1997—LNCS 1230:127-140.

*Primary Examiner* — Mia M Thomas
(74) *Attorney, Agent, or Firm* — Patterson + Sheridan, LLP

(57) ABSTRACT

In some examples, a method includes receiving a test image from a user or client, the test image depicting an anatomical region or structure of a human body, obtaining a reference image corresponding to the anatomical region or structure depicted in the test image, and analyzing the test image and the reference image to obtain a set of differences between the two images. In some examples, the method further includes, based at least in part on the set of differences, detecting a possible abnormality in the test image and outputting a result to the user or client. In some examples, a fast R-CNN is used to detecting the possible abnormality in the test image.

18 Claims, 8 Drawing Sheets

(51) Int. Cl.
  *G06F 16/538* (2019.01)
  *G06N 3/04* (2006.01)
  *G06N 3/08* (2006.01)
(52) U.S. Cl.
  CPC ........... *G06K 2209/27* (2013.01); *G06N 3/08* (2013.01); *G06T 2207/20084* (2013.01); *G06T 2210/12* (2013.01)

(56) References Cited

U.S. PATENT DOCUMENTS

| | | | | |
|---|---|---|---|---|
| 8,620,093 B2* | 12/2013 | Nguyen | ................ | G06K 9/6249 382/218 |
| 10,973,486 B2* | 4/2021 | Sjostrand | .............. | A61B 6/5223 |
| 11,037,670 B2* | 6/2021 | Colachis | ................ | G16H 20/70 |
| 2003/0202102 A1* | 10/2003 | Shiota | .............. | G08B 13/19652 348/159 |
| 2006/0098843 A1* | 5/2006 | Chew | .................... | B61L 23/041 382/103 |
| 2006/0219795 A1* | 10/2006 | Albany | .................. | G16H 10/40 235/487 |
| 2012/0106782 A1* | 5/2012 | Nathan | .................. | G08B 21/14 382/103 |
| 2015/0286868 A1* | 10/2015 | Flores | ....................... | G06T 7/38 382/103 |
| 2015/0356733 A1* | 12/2015 | Soldea | .................. | G16H 30/40 382/128 |
| 2016/0180509 A1* | 6/2016 | Sato | ......................... | G06K 9/00 382/103 |
| 2016/0291306 A1* | 10/2016 | Fukuda | ............... | G01N 15/1434 |
| 2016/0350914 A1* | 12/2016 | Champlin | ............ | G06K 9/4652 |
| 2017/0091575 A1* | 3/2017 | Lee | ........................ | G06K 9/481 |
| 2018/0137642 A1* | 5/2018 | Malisiewicz | ........ | G06K 9/4628 |
| 2018/0211380 A1* | 7/2018 | Tandon | ................. | G06K 9/6271 |
| 2018/0322327 A1* | 11/2018 | Smith | .................... | G06N 5/046 |
| 2019/0114804 A1* | 4/2019 | Sundaresan | ............. | G06K 9/66 |
| 2019/0205643 A1* | 7/2019 | Liu | ..................... | G06K 9/00624 |
| 2021/0073558 A1* | 3/2021 | Li | ............................ | G06N 3/08 |
| 2021/0082570 A1* | 3/2021 | Zhalyalov | ............. | G16H 30/40 |

* cited by examiner

REFERENCE IMAGE GUIDED OBJECT DETECTION IN MEDICAL IMAGE PROCESSING

BACKGROUND

The present invention relates to medical image processing, and more specifically to a reference guided network for object detection in medical image processing.

Medical imaging involves forming visual representations of the internal parts of a body for scientific analysis and medical diagnosis and intervention. Generally human specialists read and interpret medical images, such as, for example, radiologists. However, as multiple imaging studies for diagnosis, treatment and follow-up become standard procedure, the sheer volume of images needing to be read and interpreted has been growing exponentially. This is costly. Moreover, when a human interprets a medical image there is some subjectivity involved. Thus, when images, say in a radiology department of a clinic, are read by different technicians or radiologists, there is often inconsistency of findings.

There are many applications in the medical image processing domain, including object detection, segmentation, registration, and other tasks. There are also many imaging modalities, including, for example, X-ray, Ultrasound, Computed Tomography (CT), Magnetic Resonance Imaging (MRI), Positron Emission Tomography (PET), and others. One or more of these imaging modalities may be used in each of several anatomical or systemic areas, such as, for example, neural, retinal, pulmonary, mammary, cardiac, abdominal, and musculoskeletal regions and structures. Thus, there are complicated medical image applications for several anatomical, systemic and body parts, as well as multiple screening types.

Thus, it is useful to provide improved medical image analysis techniques to improve consistency and lessen the cost of human resources in this field.

SUMMARY

According to one embodiment of the present disclosure, a method is provided. The method includes receiving a test image from a user or client, the test image depicting an anatomical region or structure of a human body, and obtaining a reference image corresponding to the anatomical region or structure depicted in the test image. The method further includes analyzing the test image and the reference image to obtain a set of differences between the two images, and, based, at least in part, on the set of differences, detecting a possible abnormality in the test image. The method still further includes outputting a result to the user or client.

According to a second embodiment of the present disclosure, a system is provided. The system includes a user interface configured to receive a test image and provide a result to a user or client, the test image depicting an anatomical region or structure of a human body. The system further includes a reference image pairer, coupled to the user interface, configured to access a reference image database, pair the test image with a reference image from the database and register the two images, and a difference analyzer, coupled to the reference image pairer, configured to obtain a set of differences between the two images. The system still further includes an object detector, coupled to the difference analyzer and to the user interface, configured to detect, based at least in part on the set of differences, a possible abnormality in the test image.

According to a third embodiment of the present disclosure, a computer-readable storage medium is provided. The computer-readable storage medium has computer-readable program code embodied therewith, the computer-readable program code executable by one or more computer processors to perform an operation. The operation includes to receive a test image from a user or client, the test image depicting an anatomical region or structure of a human body, and to obtain a reference image corresponding to the anatomical region or structure depicted in the test image. The operation further includes to analyze the test image and the reference image to obtain a set of differences between the two, and, based, at least in part, on the set of differences, detect a possible abnormality in the test image. The method still further includes outputting a result to the user or client.

DETAILED DESCRIPTION

Figure 1:
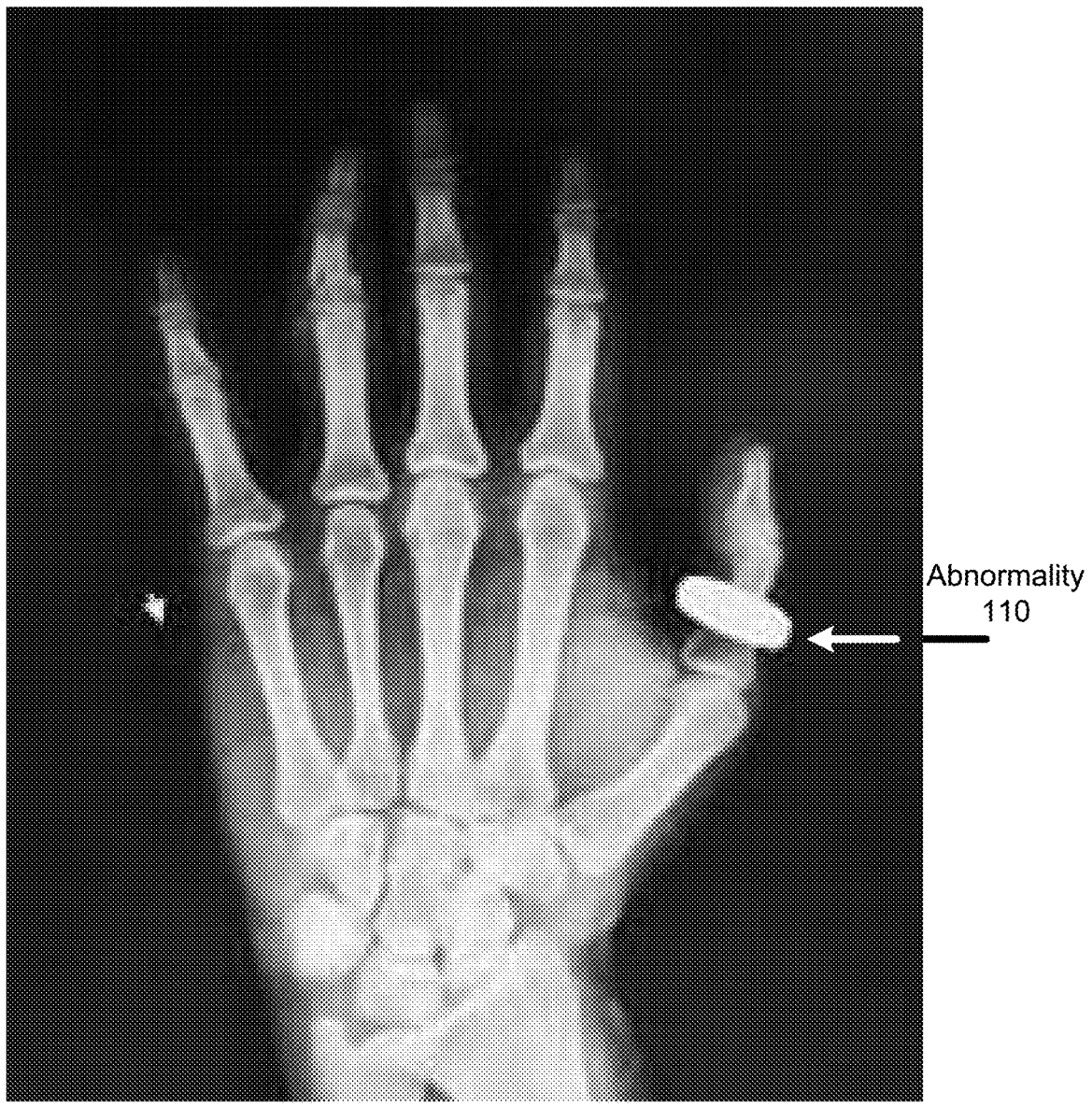
FIG. 1 illustrates a test image depicting an example left human hand with a fracture of the thumb, according to one embodiment disclosed herein.

Embodiments and examples described herein relate to reference image based object detection in a test image that has been submitted by a user or a client. It is noted that the term "test image", as used in this disclosure, refers to an image done for the purposes of a medical test. The test image may be, for example, an X-ray, or an image from a CT scan, or an MRI. In such examples automated processes may be used to detect abnormalities in such test mages. In such examples, a database of reference images for each anatomical system or organ may be maintained, each illustrating a normal condition of the depicted anatomical area, specific to a given age and gender, and optionally body type including height and weight. For example, there may be a series of reference X-ray images of the human hip and pelvis for each of several ages for each of male and female subjects. These images represent a normal, or healthy state of the pelvis for each of these respective genders and ages. For example, in the reference images database there may be X-rays of the hips and pelvis for males at ages 30, 35, 40, 45, 50, 55 and 60, as well as for ages 63, 66, 69, 72, 75, 78, and then also for each of ages 80 through 90. In one or more embodiments, the increments in years between sequential reference images shortens as the age of the subject increases, as people's bodies often change more rapidly at higher ages. There may also be, in the reference images database, a similar set of X-ray images for the female hips and pelvis at the same age increments. For each age and gender, there may also be, for example, a reference image for small, medium and large body types, based on height and weight.

Similarly, the reference image database may also include reference images, for each gender, and for several pre-defined each height and weight types, each incremented by appropriate age increments, for several other anatomical areas, systems or structures. These may include, for example, hands, wrists, feet, legs (tibia and femur), knees, lungs, neck, back and spine, etc. For anatomical areas that are gender specific, only a set of reference images specific to that anatomical area need be maintained. Thus, for diseases of the breast, such as cancer, a set of images of healthy female breasts may be included, and for diseases of the penis, scrotum and testicles a set of MRI images of healthy males may be maintained, incremented by age as well as body type, as described above.

In one or more embodiments, when a test image is received, one image from the set of reference images is used for comparison with the test image. This allows for an automated system according to one or more embodiments to focus in on an area of the test image that has some abnormality, anomaly or change from the normal, in the same manner that, for example, as would a trained human radiologist. Thus, when a human radiologist reads a test image, the first thing that he or she does is to look for any abnormalities. For example, he or she scans the image, noting the parts of the image that show normal healthy tissue and structures. Normal and healthy tissue and structures are generally not of interest in diagnosis, so those are genuinely ignored after being confirmed as normal. What the radiologist does next is to mentally identify areas of the test image that have suspicious, or out of the ordinary, information, and mentally, or even physically, draw a border around the area of interest. Having identified each such area of interest in the image, the radiologist then determines what the abnormal region of the test image indicates. Thus, the radiologist mentally detects objects in the areas of interest that have medical and diagnostic significance, and focuses his or her inquiry on those regions of interest, essentially mentally discarding the regions of the test image that show normal structures and tissue.

Figure 2A:
FIG. 2A illustrates an example reference image depicting the bones of a normal human left hand, according to one embodiment disclosed herein.
Figure 2B:
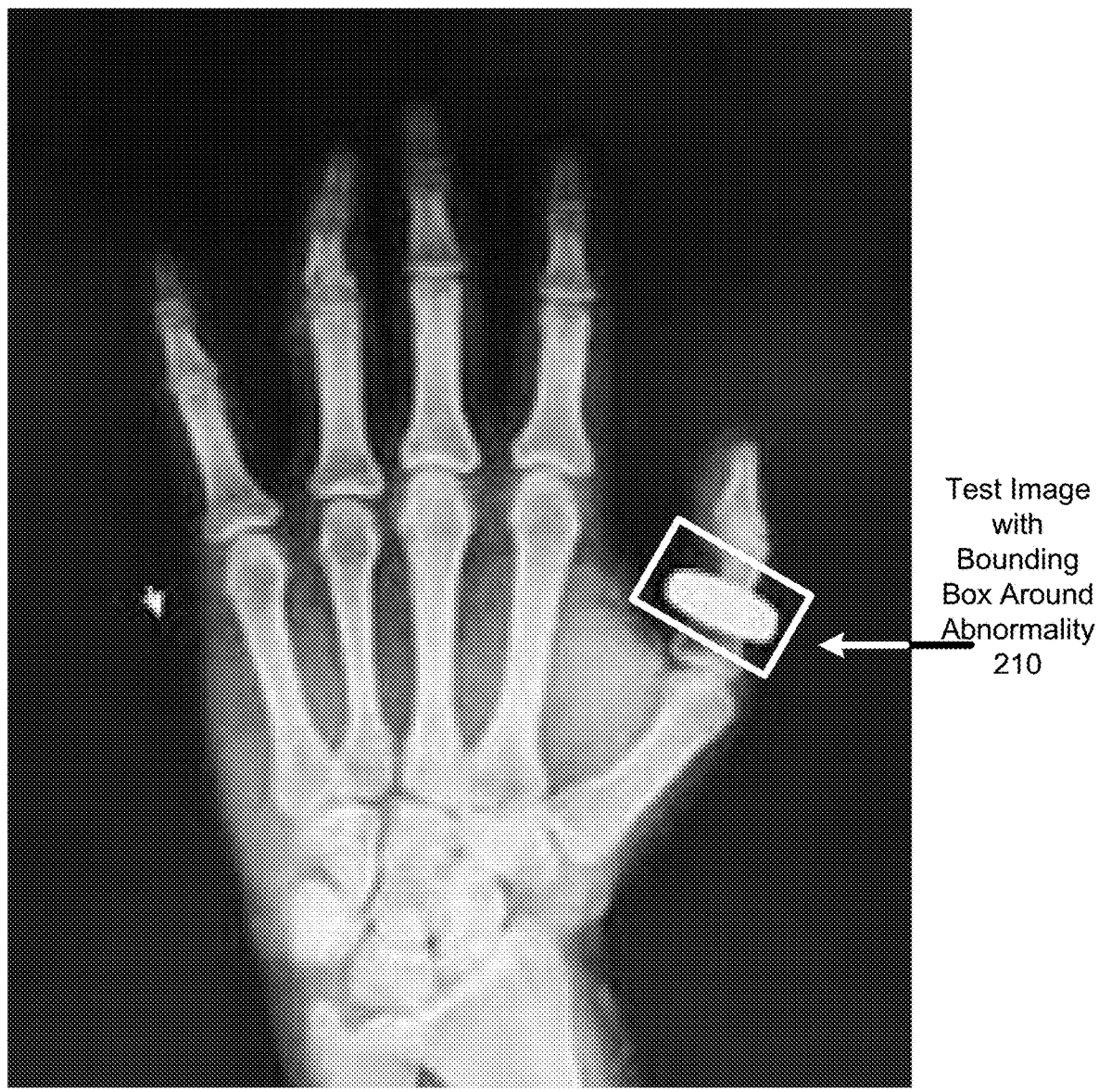
FIG. 2B illustrates the example test image of FIG. 1 with a bounding box (white) drawn around the abnormality, in this case a fracture of the thumb, according to one embodiment disclosed herein.

In one or more embodiments, this approach to test image reading and interpretation, including the detection of objects having diagnostic significance, may be automated using artificial intelligence (AI), using example systems as are illustrated, for example, in each of FIGS. 3, 4 and 5, described below. However, prior to describing the example system and system node of FIGS. 3 and 4, and the alternate system schematic drawing of FIG. 5, respectively, first, so as to provide context to the present disclosure, example test and reference images for an example anatomical area are described. These are shown in FIGS. 1, 2A and 2B, for the human left hand, respectively. These images are next described.

FIGS. 1, 2A and 2B present example test, reference and output images, in accordance with one or more embodiments. With reference to FIG. 1, a CT image of a human left hand is depicted. This image is the result of an imaging study or "test" ordered for an example patient, and is thus referred to herein as a "test image." As shown, there is an abnormality 110, namely a fracture of the thumb, that shows up as a thick white oval shape perpendicular to the bones of the thumb. In one or more embodiments, the test image of FIG. 1 may be compared to a reference image to capture any differences between the two. FIG. 2A illustrates such an example reference image, also a CT image depicting the bones of a human left hand, according to one embodiment disclosed herein. However, with reference to FIG. 2A, and in contrast to the test image of FIG. 1, the patient's thumb has no fracture or other abnormality. In fact, the reference image of FIG. 2A has no abnormalities at all, and is thus an image of a normal human left hand that may be used as a benchmark, or point of comparison, in accordance with one or more embodiments.

As described more fully below, FIG. 2B is the original test image of FIG. 1 after processing by an example system according to one embodiment disclosed herein. Thus, FIG. 2B is an output image provided by an example system, and includes a system added bounding box 210 around the abnormality, shown in FIG. 2B as a white box, which is one part of an example result provided to a user of the example system, according to one embodiment disclosed herein.

In one or more embodiments, a system and method for reference guided object detection in medical images is provided. Thus, in such embodiments, an integrated method of healthcare image analysis is provided, the method including pairing or associating a reference image from a pool of reference images with a test image submitted by a user or client. The reference image pool includes images of normal anatomical structures, which thus provide a reference of normalcy for every test image. In one or more embodiments, a differential network may also be provided to extract one or more regions of interest by determining difference information between the reference image and the original test image. Finally, in one or more embodiments, a reference guided network may be provided, being an end-to-end framework to perform object detection in each of the one or more regions of interest.

Figure 3:
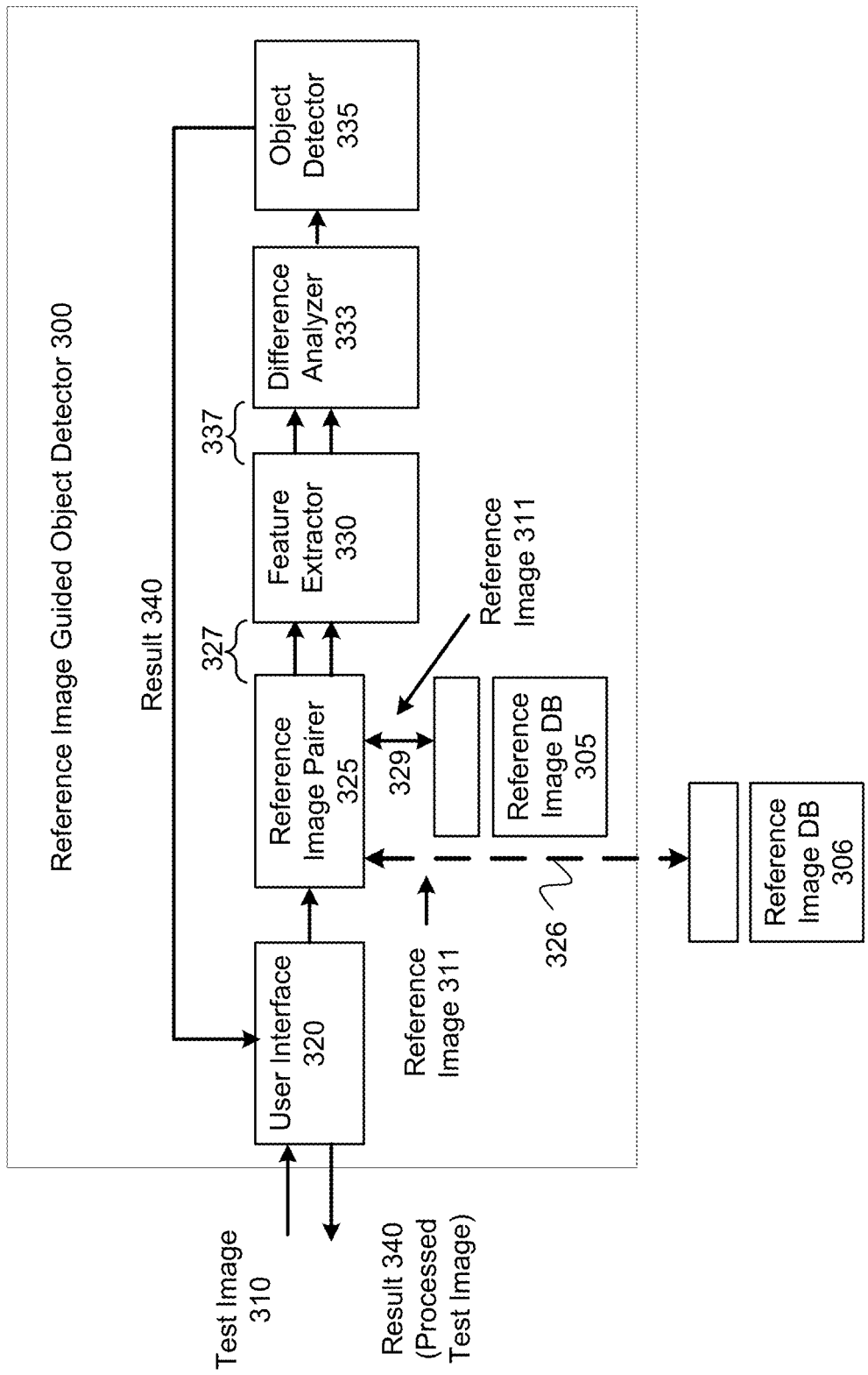
FIG. 3 illustrates a schematic drawing of an example system, according to one embodiment disclosed herein.

FIG. 3 illustrates a schematic drawing of an example system, according to one embodiment disclosed herein. As shown, the system is described as reference image guided object detector 300. With reference to FIG. 3 there is shown a user interface 320 which receives a test image 310. Test image 310 may be received, for example, from a user, such as, for example, a physician, nurse, or imaging technician in a clinic or hospital, who sends a soft copy of a recently acquired patient image to the example system. Alternatively, test image 310 may be automatically sent by an imaging system or device, such as, for example, an X-ray machine, a CT machine, an MRI machine or an ultrasound machine, to a network in a hospital or clinic that automatically sends all images to an example system for AI based reading and object detection. In the latter case, the user interface 320 may be, or may include, an application programming interface (API) through which the imaging machines may communicate with an example reference image guided object detection system, without humans being required to submit a test image 310, or to receive a result 340 in a folder of a workstation of a health care professional that is managing the care of a patient. In one embodiment, the test image 310 may be the test image of a human left hand with broken thumb, as shown in FIG. 1.

Continuing with reference to FIG. 3, once a test image 310 is received at user interface 320, it is passed to reference image pairer, which is configured to select an appropriate reference image 311 from a reference image database, to pair with test image 310, and to register the two respective images. The reference image database (DB) may be integrated with system 300, such as is, for example, reference image DB 305, and the reference image thus obtained over internal link 329, or it may be remote from system 300, such as is reference image DB 306, and thus the reference image accessed over communications link 326, for example. It is important that as part of the selection of reference image 311, that one or both of the test image and the reference image be processed so that the two images are registered, which translates the test image to have the same size and same structure as the reference image. It is only after such registration, that the difference between them can be calculated.

In some embodiments, for example those where images from imaging machines are automatically sent to an example reference image guided object detection system, there may be protocols for image acquisition that always orient each image in the same manner. In such example embodiments, where the test images are acquired to match the image registration of the reference images, it may not be necessary for reference image pairer to register the two images, or there may be only minute adjustments required, to bring the two images into registration.

Once the reference image 311 is selected by reference image pairer 325, and both text image 310 and reference image 311 have been registered, both test image 310 and reference image 311 are sent to feature extractor 330, over dual communications links 327. Feature extractor 330, which may be, for example, implemented as a convolutional neural network (CNN), extracts a set of features of each of test image 310 and reference image 311. For example, using the example of FIGS. 1 and 2A, the feature sets would include the bones of each of the five fingers of the left hand. However, in addition, the feature set extracted from FIG. 1, the test image, would also include a fracture as part of the features of the thumb.

Continuing with reference to FIG. 3, the two respective feature sets are sent over dual communications links 337 to difference analyzer 333, which determines differences between the respective feature sets extracted by feature extractor 330. Thus, for example, again using the example of FIGS. 1 and 2A as test image 310 and reference image 311 respectively, the sole difference between the two images being the fracture in the thumb of the test image, difference analyzer would output this feature, and the corresponding region of test image 311 that contains it, as result 340 to the user. In alternate embodiments (not shown), it is not necessary to have a feature extractor, and the two images themselves may be directly forwarded to difference analyzer 333, which may, in such embodiments, either calculate a pixel by pixel difference between the test image and the reference image, or calculate a distance between the test image and the reference image using some distance metric. In embodiments where the difference is directly calculated pixel by pixel, the difference image appears as a grayscale image, where a dark color portion is a difference region, and a light color portion indicates regions of similarity. In either embodiment, as noted above, it is the difference between the two respective images that embodies the abnormality, which may be a relative defect (e.g., the test image has less tissue than a normal reference image), as in the case of, for example a moth eaten bone lesion of a human hip, or which may be a relative addition, such as an osteoblastic bone lesion, for example, where there are growths not seen in a normal reference image of the same anatomical area. Or, for example, the difference may be a fracture of a bone, such as a fracture of the left thumb, as shown in FIG. 1.

Continuing further with reference to FIG. 3, once the differences between the test image and the reference image are known, it remains to detect which objects are included in the abnormality indicated by such differences. Thus, in one or more embodiments, the output of difference analyzer 333 is input to object detector 335. In one or more embodiments, object detector 335 may include, or may be implemented as, for example, either a region-based convolutional neural network (R-CNN), or a fast R-CNN. A fast R-CNN is one that combines certain elements of a standard R-CNN, namely a CNN, a support vector machine (SVM), and a bounding box regressor, into a single architecture, whereas a standard R-CNN utilizes these elements as separate architectures.

In either case, object detector 335 is trained to recognize the one or more objects in a region of interest (ROI) containing the abnormality shown in the test image detected by the difference analyzer, and, in one or more embodiments, also calculate a statistical probability that the abnormality is, in fact, the object determined by the object detector 335. The one or more identified objects, along with their probability scores, such as a percentage confidence rating, are then provided as result 340 to user interface 320, to be output to a user. As noted above, in settings where some or all medical images are routinely sent to an example reference image guided object detector 300, the user interface 320 includes an API that simply saves the result 340 to a folder in a health care professional's computer or workstation, or, for example, emails the result 340 to that health care professional. In one or more embodiments, the result may, in addition to an identification of one or more objects, and associated confidence measures of the accuracy of the respective identifications, also include the original test image with a bounding box now drawn around the ROI containing the now identified abnormality. An example of this is shown in FIG. 2B, where a white bounding box is drawn around abnormality 210 which is, as noted, a fracture of the thumb. In alternate embodiments, the bounding box may be of any desired color that is easy for a user to identify, such as, for example, red.

Figure 4:
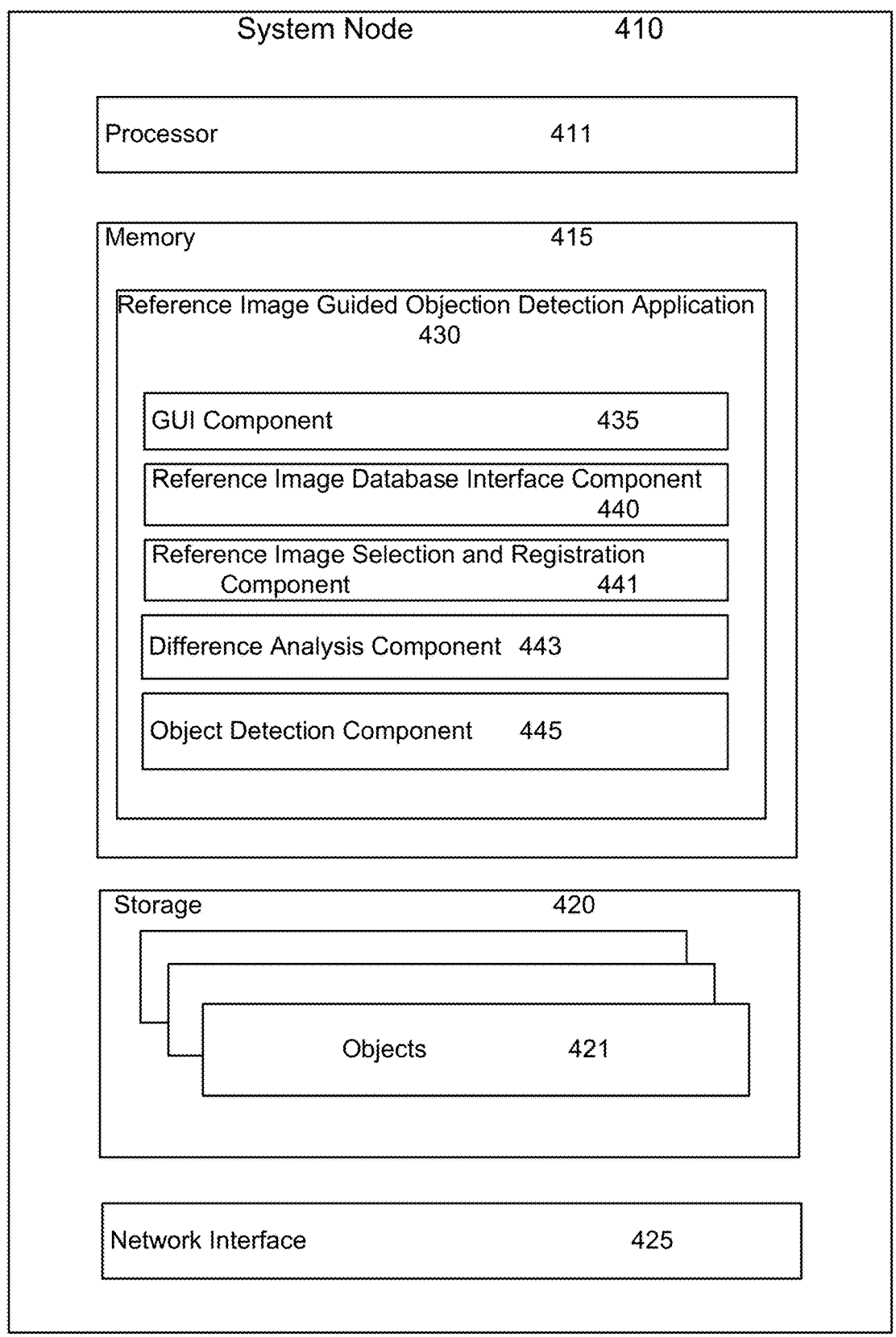
FIG. 4 is a block diagram illustrating a system node configured to provide reference image guided object detection, according to one embodiment disclosed herein.

FIG. 4 is a block diagram illustrating a System Node 410 configured to provide reference image guided object detection for medical images, according to one embodiment disclosed herein. System Node 410 is equivalent to the example system 300 schematically depicted in FIG. 3, but, for ease of illustration, without showing in FIG. 4 all of the various internal (or external) communications pathways that are shown in FIG. 3. In the illustrated embodiment, the system node 410 includes a processor 410, memory 415, storage 420, and a network interface 425. In the illustrated embodiment, the processor 410 retrieves and executes programming instructions stored in memory 415, as well as stores and retrieves application data residing in storage 420. The processor 410 is generally representative of a single CPU, multiple CPUs, a single CPU having multiple processing cores, and the like. The memory 415 is generally included to be representative of a random access memory. Storage 420 may be disk drives or flash-based storage devices, and may include fixed and/or removable storage devices, such as fixed disk drives, removable memory cards, or optical storage, network attached storage (NAS), or storage area network (SAN). Storage 420 may include one or more data bases, including IASPs. Via the network interface 425, the system node 410 can be communicatively coupled with one or more other devices and components, such as other system nodes 410, monitoring nodes, storage nodes, and the like.

In the illustrated embodiment, storage 420 includes a set of objects 421. Although depicted as residing in Storage 420, in embodiments, the objects 421 may reside in any suitable location. In embodiments, the Objects 421 are generally representative of any data (e.g., application data, saved files, databases, and the like) that is maintained and/or operated on by the system node 410. Objects 421 may include one or more artificial neural networks (ANNs), one or more convolutional neural networks (CNNs), one or more fully convolutional networks (FCNs), one or more R-CNNs, or one or more fast R-CNNs, or the like, which are trained to, and then used to, for example, extract feature maps form each of a test image and a reference image, or, for example, detect objects in one or more ROIs of the test image, as described above. Objects 421 may also include a set of reference images, used to pair with, and then be compared with, a received test image, according to some embodiments described herein. Objects 421 may still further include a set of training data used to train any or all of the neural networks described above, and used by one or more of difference analysis component or object detection component 445 of reference image guided object detection application 430, as described more fully below. As illustrated, the memory 415 includes a reference image guided object detection application 430. Although depicted as software in memory 415, in embodiments, the functionality of the reference image guided object detection application 430 can be implemented in any location using hardware, software, firmware, or a combination of hardware, software and firmware. Although not illustrated, the memory 415 may include any number of other applications used to create and modify the objects 421 and perform system tasks on the system node 410.

As illustrated, the reference image guided object detection application 430 includes a graphical user interface (GUI) component 435, a reference image database interface component 440, a reference image selection and registration component 441, a difference analysis component 443, and an object detection component 445. Although depicted as discrete components for conceptual clarity, in embodiments, the operations and functionality of the GUI component 435, the reference image database interface component 440, the reference image selection and registration component 441, the difference analysis component 443, and the object detection component 445, if implemented in the system node 410, may be combined, wholly or partially, or distributed across any number of components. In an embodiment, the reference image guided object detection application 430 is generally used to analyze a test image on a per request basis and detect any possible abnormalities that may be shown in it. In an embodiment, the reference image guided object detection application 430 is also used to calculate a confidence measure for each identified abnormality, and output results including each identified abnormality and its associated confidence measure. In an embodiment, the results also include the original test image with a bounding box drawn around a region of the test image that contains an identified abnormality.

In an embodiment, the GUI component 435 is used to provide user interfaces to communicate with users or client devices, so as to receive test images and requests to analyze them, and to provide responses to those user or client requests in the form of results respectively regarding the test images. In some embodiments, the GUI component 435 is an API that is automatically accessed by a client application to submit test images directly from imaging devices, e.g., test images depicting anatomical systems, regions or structures of a human patient of a health care professional, and, in return, receive the results of any detected abnormalities in each received test image.

In the illustrated embodiment, the reference image selection component 441, after receiving a test image form the GUI interface component 435, accesses, via the reference image database interface component 440, at least one reference image database to select a corresponding reference image to pair with the received test image. In embodiments, the database of reference images includes multiple images corresponding to the anatomical region or structure depicted in the test image, the subjects of the multiple images differentiated by at least one of age, gender and body type. In embodiments, this selection may include finding a closest match of a set of metadata of the test image to metadata of respective reference images stored in the database of reference images. In some embodiments, following selection of the reference image to pair with the input test image, the two respective images are registered. This process involves translating the test image to have the same size and same structure as the reference image. It is only after such registration, that the difference between them can be calculated. In alternate embodiments, for example, where the pool of reference images has images at different registrations or orientations, the orientation of the reference image may be a factor in its selection, so as to minimize the processing to register the test image to it.

In embodiments, the difference analysis component 443 calculates a set of differences between the test image and the selected reference image. In embodiments, to obtain the set of differences may include calculating a pixel by pixel difference between the test image and the reference image, or, for example, calculating a distance between the test image and the reference image using a pre-defined distance metric. Based on the set of differences, and in particular the regions of the test image where these differences are provided, in embodiments, the object detection component 445 performs object detection to identify any possible abnormalities in these regions, and, together with the identification of the possible abnormality, generate a confidence measure as to the accuracy of the identification. In embodiments, the confidence measure may be a probability percentage that the identification is accurate and correct.

In embodiments, System Node 410 may communicate with both users, clients and cloud servers, in which cloud based reference images databases, as well as test images are stored, via Network Interface 425.

Figure 5:
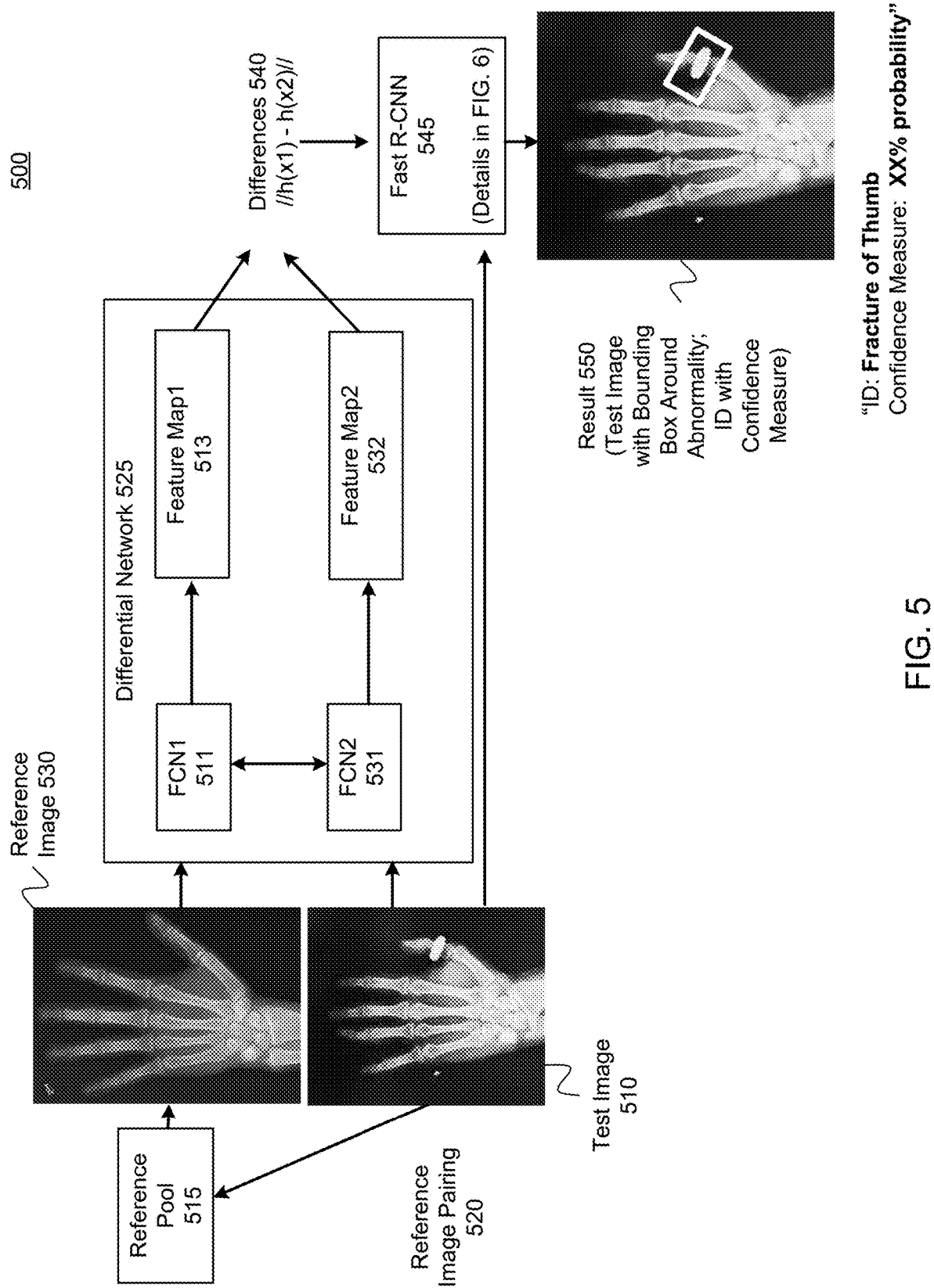
FIG. 5 illustrates an alternate schematic drawing of a system for detecting objects in medical test images, according to one embodiment disclosed herein.

FIG. 5 illustrates an alternate schematic drawing of a system 500 for detecting objects in test medical images, using a reference image guided technique, according to one embodiment disclosed herein. The example system illustrated in FIG. 5 is an alternative example to that of the system illustrated in FIG. 3, and shows example implementations for the feature extractor 330, difference analyzer 333 and object detector 335 of the example system of FIG. 3.

With reference to FIG. 5, as an example, the two images respectively shown in FIGS. 1 and 2A are provided as test image 510 and reference image 530, as shown. These images are shown in a much smaller view than in FIGS. 1 and 2A, respectively, given the spatial constraints of FIG. 5.

Continuing with reference to FIG. 5, test image 510, once received, is paired with reference image 530, selected from a reference image pool 515, which is a database maintained for example system 500 to access, as shown at reference image pairing 520. Once reference image 530 has been selected and paired with test image 510, both images are then input to differential network 525, which includes a pair of fully convolutional networks (FCNs) to extract a feature set from each of test image 510 and reference image 530. Thus, test image 510 is input to FCN1 531, which outputs feature map2 532, and similarly, in parallel, reference image 530 is input to FCN1 511, which outputs feature map1 513. The two feature maps, feature map1 513 and feature map2 532 are subtracted one from the other by differential network 525 to obtain differences 540, as shown. Differences 540 are then input into fast R-CNN 545, which performs object detection based on the regions of test image 510 implicated by differences 540. In one embodiment, fast R-CNN 545 then outputs a result 550, which has three components: the original test image as received by the example system 500, after the addition of a bounding box around the detected abnormality, an identification of the abnormality, in this example a fracture of the thumb, and a confidence measure of XX % that the identification of the abnormality is accurate. As shown, for example, the result, in addition to the image with bounding box may read:

ID: Fracture of Thumb

Confidence Measure: XX % probability.

Figure 6:
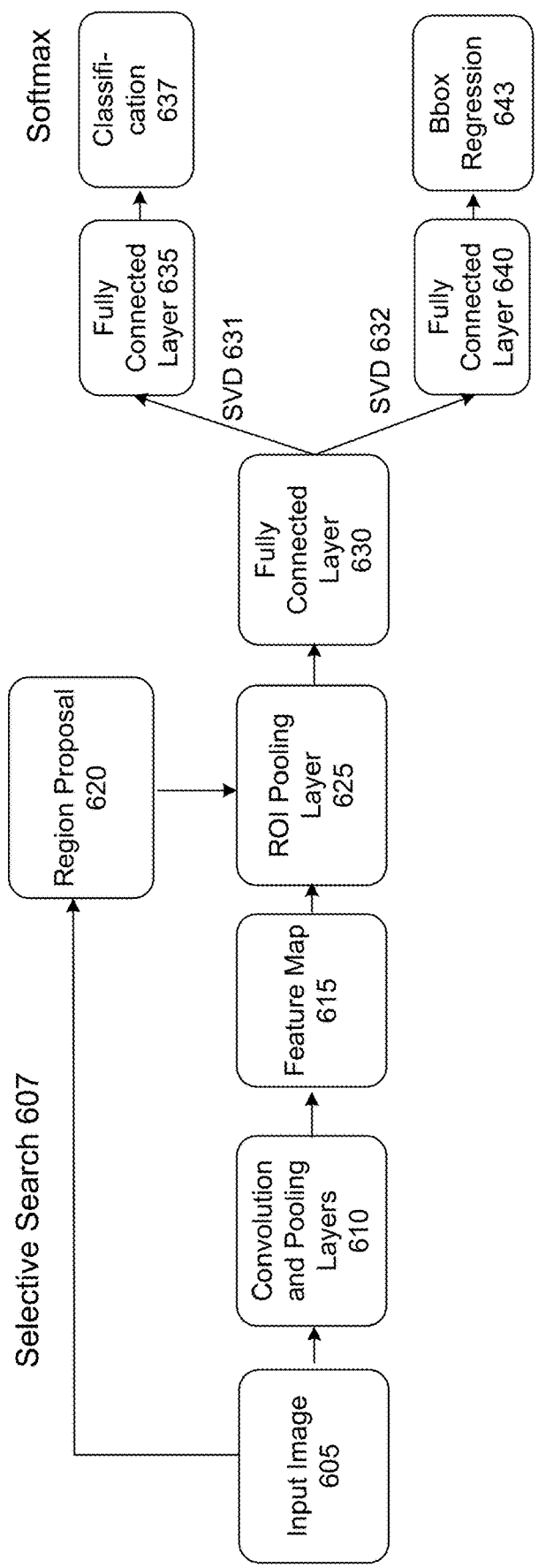
FIG. 6 depicts an example processing pipeline of the fast region-based convolutional neural network (R-CNN) shown schematically in FIG. 5.

FIG. 6 depicts process flow details of the fast region-based convolutional neural network (R-CNN) shown schematically in FIG. 5. As shown, there is a standard pipeline for a fast R-CNN.

With reference to FIG. 6, the input image 605 is the test image 510 of FIG. 5. This input image is then fed to the convolution and pooling layers 610, and a feature map 615 is extracted. Feature map 615 is input to the ROI pooling layer 625, as is the region proposal 620, which is the same as differences 540 shown in FIG. 5. As shown, because there may be several possible regions of interest (possible abnormalities), a selective search 607 is performed on the input image 605 (test image 510 of FIG. 5), to obtain the region proposals 620.

Continuing with reference to FIG. 6, the output of ROI pooling layer 625 is input to fully connected layer 630, whose output splits into two processing paths, shown as an upper path and a lower path in FIG. 6. Each path, as shown, performs a singular value decomposition (SVD). The upper path, SVD 631, includes the processing blocks fully connected layer 635 and classification 637, which identifies the abnormality in each proposed region of interest, together with a confidence measure as to the accuracy of the identification. In one embodiment, as shown, classification 637 utilizes softmax, which is a standard activation function in a classification layer of deep learning framework classification. For example, looking at the test image 510, which is input image 605 of FIG. 6, the classification processing block identifies the abnormality located in the portion of the image that depicts the top of the thumb as a fracture, and also calculates how likely the identified area is to be an actual fracture of the upper portion of a human thumb. At the same time, in the lower processing path, SVD 632, there are the processing blocks fully connected layer 640 and bounding box regression 643. Bounding box regression determines the placement of the bounding box which is output, and superimposed on the original test image, as part of the result to the user, as described above.

Figure 7:
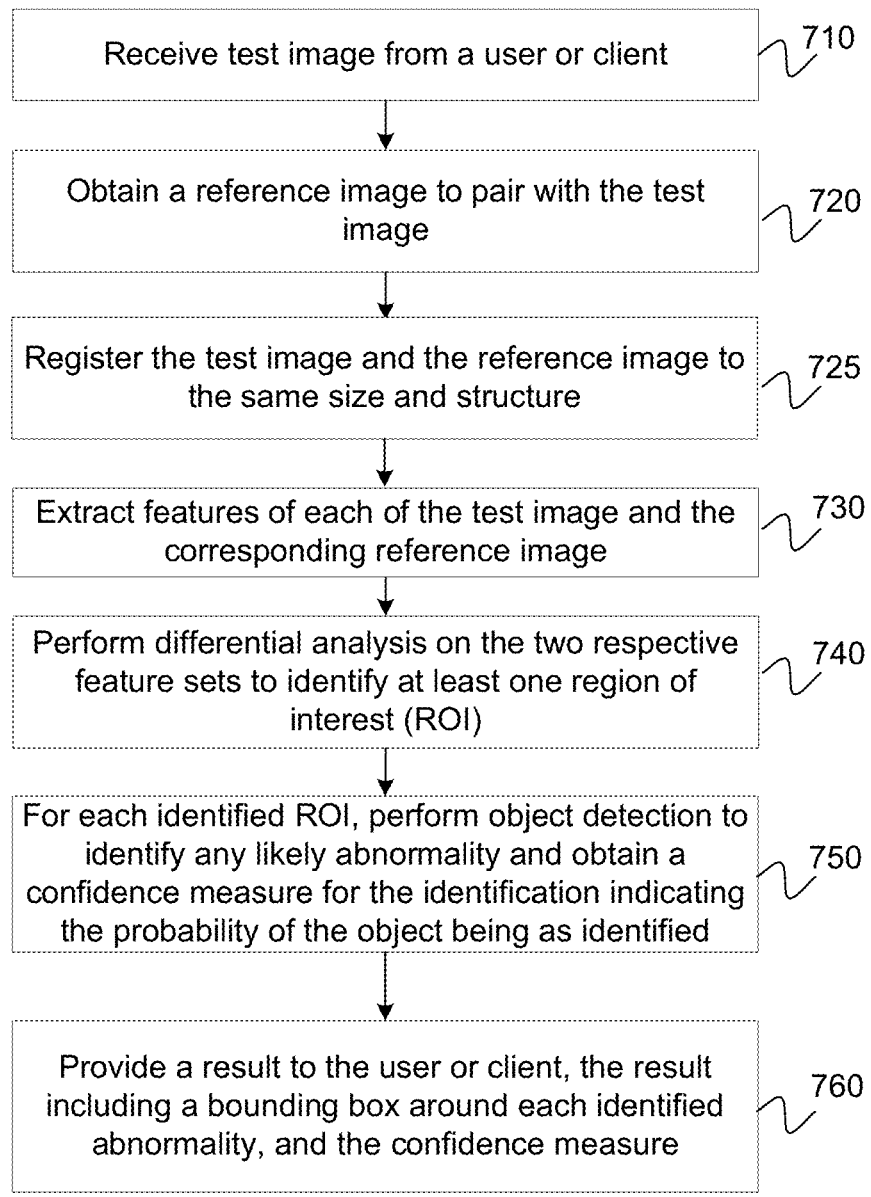
FIG. 7 depicts process flow of an example reference image based object detection method, according to one embodiment disclosed herein.

FIG. 7 depicts process flow of an example reference image based object detection method, according to one embodiment disclosed herein. FIG. 7 thus illustrates a method 700 to automatically detect an abnormality in a test image of a patient, for example, according to one embodiment disclosed herein. Method 700 includes blocks 710 through 760. In alternate embodiments, method 700 may have more, or fewer, blocks. In one embodiment, method 700 may be performed, for example, by reference image guided object detector 300 of FIG. 3, or, for example, by system node 410 of FIG. 4.

Continuing with reference to FIG. 7, method 700 begins at block 710, where a test image is received from a user or client. The test image may be, for example, the image shown in FIG. 1, for example, as described above.

From block 710 method 700 proceeds to block 720, where a reference image is obtained to pair with the test image. For example, the reference image may be selected from a reference image pool or database, either co-located with, or remote from, an example reference image guided object detection system, according to one or more embodiments disclosed herein. The selected reference image is then paired with the received test image.

From block 720, method 700 proceeds to block 725, where the test image and reference image are registered to the same size and structure, as described above. The registration allows differences between the two images to be accurately calculated.

From block 725, method 700 proceeds to block 730, where respective features of each of the test image and the selected reference image, now paired with the test image, are extracted. It is expected that the respective features of the two images will have a significant overlap, and only certain specific areas of the two images will differ in their respective characteristics, these being where the test image has some abnormality due to disease or trauma, such as, for example, a bone fracture.

From block 730, method 700 proceeds to query block 740, where a differential analysis is performed on the two respective feature sets to identify at least one ROI. The ROIs are precisely those regions where the two respective feature sets, and thus the two respective images, differ, and thus where the test image contains or indicates a possible abnormality. For example, as noted above, in the example of FIGS. 1 and 2B, the ROI would be the upper portion of the patient's thumb, such as that shown within the example white bounding box in FIG. 2B. It is this ROI that shows a different image for the upper portion of the patient's thumb.

From block 740, method 700 proceeds to block 750, where, for each identified ROI, object detection is performed to identify any likely abnormality. For example, an R-CNN or a fast R-CNN, as shown in FIG. 6, for example, may be used to detect objects within each ROI identified in block 740. Because machine intelligence may not be able to detect every object in an ROI of a test image, and, of those which it does detect, in some cases the identification may have a greater degree of confidence than others, in addition to the detection of an object a confidence measure is also provided. This is provided by a standard R-CNN, such as the example R-CNN illustrated in FIG. 6. In that example R-CNN, the bounding box is generated by processing block 643, and processing block 637 generates the confidence measure.

Finally, from block 750, method 700 proceeds to block 760, where a result is provided to the user or client, the result including the original test image with a bounding box drawn around each identified abnormality, the identification of the abnormality, and the confidence measure. Method 700 then ends at block 760.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding, reference is made to embodiments presented in this disclosure. However, the scope of the present disclosure is not limited to specific described embodiments. Instead, any combination of the features and elements discussed above, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the aspects, features, embodiments and advantages described herein are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications that perform reference image guided object detection in the cloud. Each health care professional interacting with a given patient could, for example, order several imaging studies, and obtain the resulting test images. He or she may further then access those test images and send them to the reference image guided object detection application via a user interface, or, for example, by having them automatically sent to the could based reference image guided object detection system from the devices and systems that acquire the test images. For example, the reference image guided object detection application could execute on a computing system in the cloud and store both all test images sent to it, and all results generated by it, at a storage location in the cloud. It may also store one or more databases of reference images in the cloud as well, at either a local or a remote location relative to the servers hosting the reference image guided object detection application. Doing so allows a user or client to access the results from any computing system attached to a network connected to the cloud (e.g., the Internet), and thus facilitates a central depository of all of a patient's test images and the results of object detection performed on them. In one or more embodiments, for example, the reference image guided object detection application may also send the results generated by it to a user or client system, as described above.

While the foregoing is directed to embodiments of the present invention, other and further embodiments of the invention may be devised without departing from the basic scope thereof, and the scope thereof is determined by the claims that follow.

What is claimed is:

1. A method comprising:
   receiving a test image from a user or client, the test image depicting an anatomical region or structure of a human body;
   obtaining a reference image corresponding to the anatomical region or structure depicted in the test image;
   analyzing the test image and the reference image to obtain a set of differences between the test image and the reference image; and
   based at least in part on the set of differences, detecting a possible abnormality in the test image and outputting a result to the user or client, wherein the result includes the test image with an added bounding box around an area of the test image containing the possible abnormality.

2. The method of claim 1, wherein the result further includes an identification of the possible abnormality in the bounding box.

3. The method of claim 1, wherein the result further includes a confidence measure, the confidence measure indicating a probability that the possible abnormality is an actual abnormality.

4. The method of claim 1, wherein the reference image is stored in a database of reference images, and wherein obtaining the reference image further comprises finding a closest match of a set of metadata of the test image to metadata of respective reference images stored in the database of reference images.

5. The method of claim 4, wherein the database of reference images includes multiple images corresponding to at least one of (1) the anatomical region or structure depicted in the test image or (2) subjects of the multiple images differentiated by at least one of age, gender, or body type.

6. The method of claim 1, obtaining the set of differences further comprises at least one of:
   calculating a pixel by pixel difference between the test image and the reference image; or
   calculating a distance between the test image and the reference image.

7. The method of claim 1, wherein analyzing the test image and the reference image to obtain the set of differences comprises extracting feature maps for the test image and reference image and comparing their respective features.

8. The method of claim 1, wherein detecting the possible abnormality in the test image further comprises identifying, from the set of differences, a region of interest.

9. The method of claim 1, wherein detecting the possible abnormality in the test image further comprises locating objects in the test image using at least one of:
   a region-based convolutional neural network (R-CNN); or
   a fast R-CNN that combines a convolutional neural network, a support vector machine, and a bounding box regressor.

10. A system, comprising:
a user interface configured to receive a test image and provide a result to a user or client, the test image depicting an anatomical region or structure of a human body;
a reference image pairer, coupled to the user interface, configured to access a reference image database, pair the test image with a reference image from the reference image database and register the test image and the reference image;
a difference analyzer, coupled to the reference image pairer, configured to obtain a set of differences between the test image and the reference image;
an object detector, coupled to the difference analyzer and to the user interface, configured to detect, based at least in part on the set of differences, a possible abnormality in the test image; and
a feature extractor, coupled to the reference image pairer and to the difference analyzer, configured to extract feature maps for the test image and the reference image and to provide the feature maps to the difference analyzer.

11. The system of claim 10, wherein the object detector is further configured to output, via the user interface, a result to a user or client.

12. The system of claim 11, wherein the result includes the test image with an added bounding box of an area of the test image containing the possible abnormality; and
at least one of:
an identification of the possible abnormality in the bounding box; or
a confidence measure indicating a probability that the possible abnormality is an actual abnormality.

13. The system of claim 10, further comprising the reference image database.

14. A computer program product for model selection at an edge device, the computer program product comprising:
a non-transitory computer-readable storage medium having computer-readable program code embodied therewith, the computer-readable program code executable by one or more computer processors to:
receive a test image from a user or client, the test image depicting an anatomical region or structure of a human body;
obtain a reference image corresponding to the anatomical region or structure depicted in the test image;
analyze the test image and the reference image to obtain a set of differences between the test image and the reference image; and
based at least in part on the set of differences, detect a possible abnormality in the test image and output a result to the user or client, wherein the result includes the test image with an added bounding box around an area of the test image containing the possible abnormality.

15. The computer program product of claim 14, wherein the reference image is stored in a database of reference images, and wherein the computer-readable program code is further executable to find a closest match of a set of metadata of the test image to a corresponding metadata of respective reference images stored in the database of reference images to obtain the reference image.

16. The computer program product of claim 14, wherein the result further includes at least one of:
a confidence measure indicating a probability that the possible abnormality is an actual abnormality; or
an identification of the possible abnormality.

17. The computer program product of claim 14, wherein the computer-readable program code is further executable to extract feature maps for the test image and the reference image and to compare the feature maps of the test image and the reference image to obtain the set of differences.

18. The computer program product of claim 14, wherein detecting the possible abnormality in the test image comprises detecting objects in the test image using at least one of a region-based convolutional neural network (R-CNN) or a fast R-CNN.

* * * * *